(12) United States Patent
Dal Farra et al.

(10) Patent No.: US 7,674,451 B2
(45) Date of Patent: Mar. 9, 2010

(54) COSMETIC OR PHARMACEUTICAL COMPOSITION COMPRISING PEPTIDES, USES AND TREATMENT PROCESSES

(75) Inventors: Claude Dal Farra, Opio (FR); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 12/071,002

(22) Filed: Feb. 14, 2008

(65) Prior Publication Data

US 2008/0227725 A1 Sep. 18, 2008

Related U.S. Application Data

(62) Division of application No. 10/534,355, filed as application No. PCT/FR03/003280 on Nov. 4, 2003.

(30) Foreign Application Priority Data

Nov. 8, 2002 (FR) .................................. 02 14012
Aug. 13, 2003 (FR) .................................. 03 09889

(51) Int. Cl.
*A61K 7/06* (2006.01)
*A61K 38/00* (2006.01)
*C07K 16/00* (2006.01)

(52) U.S. Cl. ................... 424/70.1; 424/70.9; 424/70.14; 424/78.2; 424/401; 530/331; 530/333; 530/345; 514/18; 514/844; 514/887

(58) Field of Classification Search ................ 424/70.1, 424/70.9, 70.14, 78.2, 401; 530/331, 333, 530/345; 514/18, 844, 887
See application file for complete search history.

(56) References Cited

FOREIGN PATENT DOCUMENTS

| EP | 0 764 444 | 3/1997 |
|----|-----------|--------|
| FR | 2 788 777 | 7/2000 |

OTHER PUBLICATIONS

Duda Teresa et al: "Core sequence of ATP regulatory module in receptor guanylate cyclases.", FEBS (Federation of European Biochemical Societies) Letters, vol. 315, No. 2, 1993, pp. 143-148, XP002243861, ISSN: 0014-5793, p. 144, colonne de droite, dernier alinea.

*Primary Examiner*—Jon P Weber
*Assistant Examiner*—Abdel A Mohamed
(74) *Attorney, Agent, or Firm*—Young & Thompson

(57) ABSTRACT

The present invention relates to the use of at least one peptide, with the sequence (AA)n -Arg-Gly-Ser-(AA)n, where (AA) is any amino acid or one of its derivatives, and N is an integer between 0 and 3, as an active ingredient, in or for the preparation of a cosmetic and/or dermatological and/or pharmaceutical composition. The invention also relates to its use in order to treat, inter alia, the cutaneous manifestations of aging and/or its use in order to act against cellulite. The invention is, in the same way, related to a composition containing it as well as a process of cosmetic treatment of the skin using the said peptide or the said composition.

13 Claims, No Drawings

COSMETIC OR PHARMACEUTICAL COMPOSITION COMPRISING PEPTIDES, USES AND TREATMENT PROCESSES

This is a divisional of application Ser. No. 10/534,355, filed May 9, 2005, now allowed, which is a 371 National Stage application of International application Ser. No. PCT/FR2003/003280, filed Nov. 4, 2003, which claims priority to French application nos. 02/14012 and 03/09889, filed Nov. 8, 2002 and Aug. 13, 2003, respectively. The entire contents of the above-referenced applications are hereby incorporated by reference in their entirety.

The invention relates to the cosmetic and pharmaceutical field, in particular the field of dermatology. The present invention has as an aim a cosmetic and/or dermatological and/or pharmaceutical composition including as an active ingredient at least a peptide, with the sequence (AA)n-Arg-Gly-Ser-(AA)n, in which (AA) is any amino acid or one of its derivatives, N ranging between 0 and 3.

BACKGROUND OF THE INVENTION

The skin is a coating organ covering the totality of the body's surface. It is a vital organ ensuring multiple functions such as sensitive functions, protective functions from external aggressions, as well as immunological, metabolic or thermoregulatory functions. These roles are made possible due to a complex structure which associates various tissues. The skin consists of three superimposed distinct layers: epidermis, dermis and hypodermis. The epidermis is a coating epithelium which constitutes the external structure of the skin and provides its function of protection. This function is provided by the cohesion of the epithelial cells and by the production of a filamentous and resistant protein, keratin.

The dermis is a connective tissue made up of a ground substance in which fibroblasts reside along with collagen fibers and elastin fibers, which are fibrous protein synthesized by fibroblasts. The collagen fibers ensure a great part of the solidity of the dermis, they take part in the elasticity and especially in the tonicity of the skin and/or the mucous membranes.

Below the dermis is a layer of adipose tissue: hypodermis. The hypodermis consists of a reserve fat layer, or white adipose tissue, attached to the lower part of the dermis by expansions of collagens and elastic fibers. It consists of large vacuolated cells, the adipocytes, almost entirely filled with triglycerides. The volume of these cells can change rapidly, during a weight loss or weight gain, and can measure from 40 to 120 μm in diameter, which corresponds to a variation of 27 times in volume. The adipose tissue also contains connective tissue in which we can find, inter alia, particular fibroblasts and preadipocytes. The adipose tissue can store lipids as triglycerides or release them as fatty acids and glycerol.

Today, the health and cosmetics specialists use more and more means in order to discover new active ingredients which are able to act on the skin. This industry seeks active ingredients which are not only able to protect and maintain skin but also active ingredients which are able to improve its appearance as well as the well-being of the individuals who use it. It is necessary that these new products simultaneously possess several properties and that, consequently, they provide an improved spectrum of performances. Thus, these active ingredients must have a general mode of action on the skin, and must therefore act at various levels.

The purpose of this invention is to offer a new substance, usable in the fields of cosmetics and pharmaceuticals, and which presents, in addition to skin care properties, a preventive and curative action on the manifestations of cutaneous aging, as well as a stimulative and revitalizing action. Thus this active ingredient will be able to fight against the phenomena of cutaneous aging, while efficiently protecting the skin at the same time. Additionally, it will have a slimming effect.

Adenosine 5'-Triphosphate (ATP) is a molecule which plays a central role in many cellular mechanisms. It is, indeed, the principal source of energy for the cells: this molecule is capable of keeping chemical energy in reserve and easily releasing it in reactions that require energy. ATP plays an important role in the skin: it is a marker of vitality and activity of cells. For example, cell activity correlates closely with an increase in the synthesis of essential molecules, such as proteins or DNA. So, by increasing the quantity of intracellular ATP, the cell is stimulated and receives the necessary energy in order to synthesize the enzymes which will induce mechanisms of activation and which will thus make it possible to increase cellular metabolism.

Thus, for example, by stimulating molecule synthesis, essential for the healthy functioning of the skin, such as extracellular matrix proteins (collagen, elastin, fibronectin) or keratin, the skin will fight better against the phenomena of aging and promote its renewal (by increasing cell proliferation and differentiation). The skin will also be able to better develop its repair process or to fight more effectively against UV damage.

SUMMARY OF THE INVENTION

The inventors have succeeded in selecting particular substances presenting remarkable properties when they are applied to the skin. In an unexpected way, the inventors discovered that peptides corresponding to the general formula (I): (AA)n-Arg-Gly-Ser-(AA)n (I) in which (AA) is an unspecified amino acid, or one of its derivatives, and N is an integer ranging between 0 and 3, have remarkable properties as a skin care agent.

The active ingredient thus obtained has remarkable effects on the skin. In addition to its care properties, it has a true stimulating and revitalizing action on the skin and on the cells which compose it. Thus, this compound has slimming, anti-cellulite properties and protective properties, also while it has a very effective action in the fight against the manifestations of cutaneous aging. Indeed, it was discovered that this peptide has an effect on the modulation of ATP concentration in the cell, on the intracellular calcium concentration and also on the production and activation of proteins, which are essential to the skin.

DETAILED DESCRIPTION OF THE INVENTION

Firstly, the aim of the present invention is the use, as active ingredient, of at least a peptide of formula (I):

wherein (AA) is an unspecified amino acid or one of its derivatives, N is an integer ranging between 0 and 3, to be used alone or in association with at least another active agent, in or for the preparation of a cosmetic and/or dermatological and/or pharmaceutical composition.

The term "amino acid" refers here to any natural or unnatural organic acid with the following formula (II):

wherein each —R is independently selected between a hydrogen and an alkyl grouping having between 1 and 12 carbon atoms. Preferentially, at least an —R grouping of each amino acid is a hydrogen.

The term "alkyl", refers to a carbonaceous chain that can be linear or ramified, substituted (mono or poly-) or not substituted; saturated, mono-saturated (a double or triple bonds in the chain) or poly-unsaturated (two or several double bonds, two or several triple bonds, one or more double bonds and one or more triple bonds in the chain).

To the knowledge of the applicant, it has never been described in former art the use of a peptide of sequence (AA)n-Arg-Gly-Ser-(AA)n in which (AA) is an unspecified amino acid, or one of its derivatives, and N an integer ranging between 0 and 3, in cosmetics and/or dermatology and/or pharmaceuticals. The peptide used according to the invention can contain in particular from 3 to 9 amino acid residues, and in particular 3, 4 or 5 amino acid residues. In particular, the invention relates to the use of peptides containing at least the peptide sequence, Arginine-Glycine-Serine, as well as the use of derivatives from these peptides.

According to a currently preferred mode of realization, the above mentioned peptide is preferentially the peptide of Arg-Gly-Ser sequence. When one uses a peptide containing the tripeptide Arginine-Glycine-Serine, it is clearly understood that this one is selected so that the amino acids surrounding the Arginine-Glycine-Serine pattern, both by their nature and the secondary structure of peptide they will induce, do not prevent this one from carrying out the activity for which it is used in the present invention. The amino acids and the peptide derivatives are, for example, those in which at least one functional grouping (in particular the amine and carboxylic groupings) is protected with a protective grouping.

Indeed, it may be necessary, for resistance to degradation, to use according to the invention a protected form of the peptide. The form of protection must obviously be a biologically compatible form and must be compatible with cosmetic use or the field of pharmaceuticals. Many biologically compatible forms of protection can be considered, they are well known to the person skilled in the art, such as for example the acylation or the acetylation of the amino-terminal, or the amidation or the esterification of the carboxy-terminal. Thus, the invention concerns a use such as previously defined and characterized by the fact that the peptide is in a protected form or not.

Preferably, we use a protection based either on acylation or acetylation of the amino-terminal, or on the amidation or the esterification of the carboxy-terminal, or both. The amino acid and peptide derivatives also relate to the amino acids and to the peptides connected to each other with a pseudo-peptide bond. We understand by "pseudo-peptide bond" all types of bonds likely to replace the "traditional" peptidic bonds.

In the field of amino acids, the geometry of the molecules is such that they can theoretically appear as different optical isomers. There is indeed a molecular conformation of the amino acid (aa) such that it deviates the plane of polarized light to the right (dextrogyre conformation or D-aa), and a molecular conformation of the amino acid such as it deviates the plane polarized light to the left (levogyre conformation or L-aa). Nature retained for the natural amino acids only levogyreous conformation. Consequently, a peptide of natural origin will be made only with amino acids of L-aa type. However the chemical synthesis in laboratory makes it possible to prepare amino acids having the two possible conformations. From this basic material, it is therefore possible during peptide synthesis, to incorporate amino acids in the form of dextrogyre or levogyre optical isomers. Thus, the amino acids which constitute the peptide relating to the invention, can be in L- and D-configuration; in a preferential way, the amino acids are in L-form. The peptide relating to the invention can thus be in L-, D- or DL-form.

Peptides, objects of this patent, can be obtained either by traditional chemical synthesis (in solid phase or in homogeneous liquid phase), or by enzymatic synthesis (Kullman et al., *J. Biol. Chem.* 1980, 225, 8234) from constitutive amino acids or from their derivatives. Peptides relating to the invention can also be obtained by fermentation of a strain of bacteria, modified or not, by genetic engineering to produce peptides of the sequence, as previously indicated, and their fragments, or by protein extraction of animal or vegetable origin, preferentially of vegetable origin, followed by controlled hydrolysis which releases the peptide fragments of average and small sizes, on the condition that the released elements must contain at least the Arg-Gly-Ser sequence. Many proteins found in the plants are likely to contain these sequences within their structure. The spared hydrolysis makes it possible to release these peptide fragments.

It is possible, but not necessary to perform the invention, first to extract either the proteins concerned and then to hydrolyze them, or to initially perform the hydrolysis on rough extract and then to purify the peptide fragments. Other simpler or more complex processes can be considered by the person skilled in the art, knowing the work of synthesis, extraction and purification of proteins and peptides. Thus the peptide according to the invention can be a peptide of natural or synthetic origin. Preferentially according to the invention, the peptide is obtained by chemical synthesis.

According to an advantageous mode of realization of the invention, the above mentioned peptide is solubilized beforehand in one or several cosmetically or pharmaceutically acceptable solvents such as water, ethanol, propanol or isopropanol, propylene glycol, butylene glycol, dipropylene glycol, ethoxylated or propoxylated diglycols, cyclic polyols or any combinations of these solvents. According to another advantageous mode of realization of the invention, the above mentioned peptides are beforehand solubilized in a cosmetic or pharmaceutical vector such as liposomes or are adsorbed on powdered organic polymers, mineral supports such as talc and bentonites, and more generally solubilized in, or fixed on, any cosmetically or pharmaceutically acceptable vectors. It is of course obvious that the peptide according to the invention can be used alone or in partnership with at least another active agent, in or for the preparation of a cosmetic and/or dermatological and/or pharmaceutical composition.

The peptide according to the invention is used favorably as skin care product and treatment agent for the skin and/or superficial body growths. Skin care product and treatment agent refer, within the meaning of the present invention, to agents which present, in a general way, a repairing and revitalizing activity allowing, inter alia, the skin and/or superficial body growths to better react to the aggressions which they can be subjected to. This peptide acts favorably on the energy metabolism of skin cells, such as fibroblasts and adipocytes. It also possesses a cytostimulating activity.

The peptide according to the invention is used favorably as a skin care product and treatment agent for the skin and/or superficial body growths; it allows the activation of the cellular energy metabolism. By referring to agents allowing the activation of cellular energy metabolism, we refer to compounds able to increase the synthesis of intracellular ATP in skin cells or that are able to increase the intracellular calcium concentration.

Indeed, it has been shown that the peptide according to the invention makes it possible to increase the synthesis of intracellular ATP, in particular, on fibroblasts and adipocytes; but also that it is able to increase the concentration of intracellular calcium of skin cells. This stimulation allows the activation of various mechanisms favorable to the cell, in particular those which help it fight against stress and aging. The peptide according to the invention can also have an antioxydant action.

The cytostimulant and revitalizing activity of the peptide according to the invention is characterized by an increase in the differentiation and cell regeneration. Indeed, the peptide according to the invention promotes cell differentiation, in particular keratinocyte differentiation. They migrate more rapidly towards the skin's surface and ensure a better resistance by the cornea layer.

While progressing towards the superficial layers, keratinocytes are flattened and discharge a cement made up of lipids, cholesterol, saturated free fatty acids and ceramides into the extracellular space. This cement increases cohesion between the cells and thus contributes to the barrier function of the skin. The peptide efficiently increases the function of the cutaneous barrier of the skin and thus promotes tissue regeneration. The compound according to the present invention, by its cytostimulating action, will efficiently play a role in all the phenomena related to cutaneous aging and cell stress. The energy reserve constituted by the peptide according to the invention improves protein synthesis in skin cells and/or improves their stability, particularly in epidermal cells.

It was shown that the peptide, according to the invention, has beneficial effects on extracellular matrix proteins, in particular they increase and promote their synthesis. The phrase "extracellular matrix protein", refers to proteins such as collagen, fibronectin or elastin. Equally, it has been shown that the peptide of formula (I) has an effective action on keratinocytes. The invention thus has for another object, the use of at least a peptide such as previously defined, in or for the preparation of a composition, in order to stimulate keratin synthesis.

The peptide according to the invention is thus particularly well adapted to use in order to fight, in a curative and/or preventive way, the phenomena of cutaneous aging. Manifestations of cutaneous aging include all modifications regarding external appearance of skin due to aging. Examples of these modifications include wrinkles and fine lines, limp skin, slackened skin, slimmer looking skin, loss of elasticity and/or skin tone, dull skin, and skin which lacks radiance. It also includes internal skin modifications that do not translate directly into changes in the external appearance of the skin. An example of these internal modifications is the degradation that occurs internally in skin resulting from consecutive exposure to UV radiation.

The increase in ATP concentration will also allow the cell to be protected and thereby improve its ability to resist environment stress that it is subjected to. The cell will therefore be protected from all types of external aggressions. The present invention thus relates to the use of at least a peptide of formula (I) such as previously defined, in or for the preparation of a composition, in order to protect the skin and/or the hair against all types of external aggressions. The phrase "external aggressions" refers to the aggressions which the environment can produce. These aggressions can be of chemical, physical, biological or thermal origin. As an example, we can cite aggressions such as pollution, V, frictions, water with strong limestone concentration, variations in temperature or potentially irritating products such as tensioactives, preservatives or fragrances.

In addition, by its stimulative activity, the peptide has a particular and strong activity on lipolysis, which makes it particularly useful in preparations aimed at slimming. It was noted that the peptide according to the invention, or the composition containing it, has an effect on adipocytes. This peptide can be thus used in or for the manufacture of a cosmetic and/or pharmaceutical composition, for topic use, intended for the treatment of cellulite and/or the treatment of orange-peel skin.

It is used in a more general way in order to reduce, eliminate or prevent subcutaneous fat overloads. Cellulite is a particular configuration of adipose tissue. It indicates a quilted and padded skin appearance which corresponds, in a diagrammatic way, with an increase of the adipose tissue in certain areas of the body due to an increase in the quantity of fat, stored in the adipocytes, whose volume and number increase. At an advanced stage of cellulite formation, the skin spontaneously takes the appearance of "orange-peel skin".

The peptide according to the invention contributes significantly to reducing the quantity of triglycerides contained in the adipocyte vacuoles. This phenomenon is due to an increase in the phenomenon of lipolysis in the adipocytes, a mechanism which acts through an increase in the quantity of intracellular ATP followed by an increase in the quantity of intracellular cAMP. This increase in the cAMP concentration results in an increased stimulation of Triglyceride-lipase activity, an enzyme which allows the hydrolysis of triglycerides into fatty acids. Lipolysis is the reaction which eliminates triglycerides stored in the adipocytes. An increase in this phenomenon will allow a more significant elimination of triglycerides as well as an increase in the release of free fatty acid and glycerol into the extracellular medium. Thus, when the quantity of triglycerides present in the adipocyte vacuoles decreases, their volume decreases. The skin gradually takes back its "normal" appearance: the adipose tissue is reduced, the orange-peel skin effect is attenuated, the unpleasant appearance of the body disappears.

Thus, the degree of lipolyptic activity of the peptide according to the invention and its capacity to act in lipolysis will vary according to the cAMP concentration. The peptide will allow the fatty deposits to decrease, to slow down or to resorb. The active ingredient according to the invention or the composition containing it will have a slimming activity and will enable the appearance of the skin to improve and, in particular, to attenuate the appearance of "orange-peel skin".

According to another aspect, the invention relates to a cosmetic and/or dermatological and/or pharmaceutical composition characterized in that it contains, in an acceptable medium, as an active ingredient, at least a peptide of formula (I): (AA)n-Arg-Gly-Ser-(AA)n (I) in which (AA) is an unspecified amino acid or one of its derivatives, and N is an integer ranging between 0 and 3. According to a currently preferred mode of realization of the invention, the composition contains the peptide of sequence Arg-Gly-Ser.

In a more general way, the composition according to the invention contains the active compound such as defined previously. Thus, the peptide in the composition is selected among peptides from which at least a functional grouping is protected by a protective grouping. This protective grouping is either an acylation or an acetylation of the amino-terminal end, or on an amidation or an esterification of the carboxy-terminal end, or both.

It is clearly understood that the peptide according to the invention can be used alone or in association with at least another active agent. In the composition according to the invention, the peptide can be a mixture of peptide derivatives and/or consisting of amino acids derivatives. The composition containing the peptide according to the invention can be a cosmetic, dermatological or pharmaceutical composition. Preferentially according to the invention, the composition is a cosmetic composition, because it is intended to improve the appearance and the general cutaneous performances of the individual who uses it.

According to the present invention, the composition is preferably a cosmetic and/or dermatological composition adapted for topical cutaneous application through an acceptable cosmetic or pharmaceutical medium.

It is obvious that the invention relates to mammals in general, and more specifically, to humans. The effective quantity of active ingredient corresponds to the quantity necessary to obtain the desired result. Relating to an advantageous mode of realization of the invention, the above mentioned peptide is present in the compositions of the invention at a concentration from approximately 0.005 to 500 ppm (p/p), and preferentially at a concentration from approximately 0.1 to 50 ppm (p/p) compared to the total weight of the final composition.

Whatever forms the invention takes, the composition, according to the invention can be ingested, injected, or, applied to skin (on all cutaneous zones of the body), hair, nails or mucous membranes. According to the mode of administration, the composition relating to the invention can be presented under all the galenic forms normally used. Preferentially, the compositions relating to the invention are presented under a galenic form adapted for cutaneous topical administration. They include all the cosmetic and dermatological forms. These compositions must contain an acceptable cosmetic or dermatological medium, which is compatible with skin and hair. These compositions can take the form of an aqueous, hydro-alcoholic, or oil solution in oil-water emulsions, water-oil emulsions or in multiple emulsions an aqueous, hydro-alcoholic, or oily solution, oil-in-water emulsions, water-oil emulsions or in multiple emulsions. They can also be used as creams, in suspension, or as a powder, as long as it is adapted for application to skin, mucous membranes, lips and/or hair.

These compositions can also be more or less fluid and take the form of creams, lotions, milks, serums, ointments, shampoo, gel, paste and foam. It can also take a solid form such as a stick, or it can be used in aerosols. It can also be used as a skin care product and/or as make-up for skin.

Moreover, these compositions represent all additives that are usually used in this application. These compositions also represent all the possible additives necessary for their formulation such as solvents, thickeners, diluents, anti-oxidants, colorants, solar filters, self-tanning products, pigments, fillers, preservatives, perfumes, odor absorbers, pharmaceutical and cosmetic active ingredients, essential oils, vitamins, essential fatty acids, tensioactives, filmogen polymers etc. . . . In any case, specialists in their field will want to carefully consider the selection of adjuvants, as well as their proportions, so as not to compromise the advantageous properties of the composition relating to the invention. These adjuvants can, for example, correspond to 0.01% to 20% of the total weight of the composition. When the composition relating to the invention is in an emulsion, the fatty phase can represent from 5% to 80% by weight, and preferably from 5% to 50% of the weight with respect to the total weight of the composition. Emulsifiers or co-emulsifiers used in the composition are selected among those that are classically used in the domain under consideration. For example, they can be used in a proportion of 0.3% to 30% by weight relative to the total weight of the composition. Of course, the person skilled in the art should select the complementary compounds for the composition, active or non-active, as well as the amounts of the complementary compounds in such a way that the advantageous properties of the composition will not be perceptibly altered by the envisaged addition.

The compositions relating to the present invention can be applied in particular as a cosmetic or pharmaceutical composition for skin use, mucous membranes and/or semi-mucous membranes, but also as cosmetic or pharmaceutical compositions for superficial body growths and/or hair. The compositions can be applied particularly as skin protection and skin care products, or as an anti-wrinkle and/or an anti-aging composition, or as a slimming and/or toning composition.

The slimming and/or toning composition could be applied locally to the zones of the face or the body to be slimmed, in particular to the hips, the buttocks, the thighs, the belly and the face. We can also consider an application in the field of facial and body make-up compositions, such as lipsticks, foundation, tinted creams, dark circle sticks, or sunscreen and artificial tanning compositions.

The compositions of the invention can be used in a great number of treatments, notably cosmetic and dermatological treatments. They can take the form of cosmetic compositions for lips and/or hair treatment, skin protection, care and make-up removal and/or cleaning, as well as for make-up applications to skin, lips, eyelashes and/or the body. The composition relating to the invention can also consist of solid preparations such as soap and other cleaning bar soaps. The composition can also be made in aerosol form in which it can be mixed with pressurized propulsion agents. The composition can also be used orally, for example, as toothpaste.

The composition of the invention can be applied as a cosmetic, dermatological or pharmaceutical composition to be used orally. These can take the form of drinkable solutions, syrups, tablets, sugar-coated pills, capsules, or even as food and nutritional supplements. According to the invention, we can add to the composition of the invention, other active agents intended for the prevention and/or treatment of the manifestations of cutaneous aging or intended for skin protection against external aggressions, or active ingredients intended for the treatment of cellulite and the phenomenon of "orange-peel skin".

Additionally, the present invention relates to a process of cosmetic treatment intended to treat old skin and/or to fight in a curative and/or preventive way the phenomena of cutaneous aging. This consists in applying, an effective amount of a composition, such as previously defined, to the surface of the skin, i.e. a composition containing peptide corresponding to the general formula (I), in order to obtain the desired action.

The present invention also relates to a process of cosmetic treatment designed to protect the skin and/or the hair against all types of external aggression.

According to another aspect of the invention, the present invention relates to a process of cosmetic treatment in order to promote cell differentiation and/or to promote tissue regeneration and/or in order to reinforce the cutaneous barrier of the skin. This consists in applying an effective amount of a composition, such as previously defined, to the surface of the skin.

The present invention also relates to a cosmetic process in order to obtain a slimming action as well as a process of cosmetic care intended to reduce, eliminate and/or prevent overloading of subcutaneous fat, and/or intended to fight against cellulite and/or to fight against the phenomenon of orange-peel skin. This consists in topically applying an effective amount of a composition, such as previously defined, to concerned zones of the skin.

Particular modes of realization of this process of cosmetic treatment also result from the preceding description.

The process of cosmetic treatment relating to the invention can be implemented in particular by applying the cosmetic compositions here above according to methods generally used for compositions such as the application of creams, gels, serums, lotions, milks, shampoo, and sun creams, on skin, hair and as a toothpaste applied to the gums.

Other advantages and characteristics of the invention will become apparent by reading the following examples, by way of an illustrative and unrestricted demonstration of data.

EXAMPLE 1

Demonstration of the Effect of the Peptide on the Amount of Intracellular ATP The goal of this study is to determine the influence of the peptide according to the invention on ATP production by various skin cells. This study is carried out using a Kit, "ATP Bioluminescence Assay Kit HS II", which assesses the concentration of intracellular ATP. The study is carried out on fibroblasts and on a differentiated preadipocyte cell line, 3T3-L1.

Part of the test was carried out on fibroblasts. These fibroblasts were cultivated then put in culture in 12 well plates (Labtecks). When the cells reached 80% confluence, a solution containing peptide of the sequence Arg-Gly-Ser at the concentration of $10^{-6}$ M was applied to the cells for 5, 15, 30 and 60 minutes. Control tests were carried out by applying solutions without active ingredients to the cells.

The test has been made, in the same way, on cultured 3T3-L1 fibroblasts. These cells have the ability to differentiate, under the action of a hormonal cocktail, into preadipocytes, then into adipocytes filled with triglycerides. The preadipocyte cells are cultured in Labteks and are maintained up to 100% confluence in culture medium DMEM containing 10% of FCS. Once at confluence, the cells are cultivated in traditional culture medium, containing differentiation inductors (IBMX, dexamethasone and insulin), in order to induce the final phases of differentiation and to obtain mature adipocytes. The adipocytes are then treated with peptide of sequence Arg-Gly-Ser, representative of the family of peptide according to the invention, put in solution at 1% of a 50 ppm solution, or with a solution without active ingredient. The adipocytes are incubated for different times: 5 minutes, 15 minutes and 3 hours.

At the end of the time of incubation, the various plates containing the fibroblasts or the adipocytes are emptied, rinsed with 2 ml of cold PBS, after 250 ml of lysis buffer, provided by the kit, are added. The cells are then collected separately in tubes of 14 ml and each well is rinsed with 2×500 ml of cold PBS. Each tube is then placed in the polytron for 10 seconds at 18000 rpm. A dilution of 1/1200, using cold PBS, is carried out for each condition before each reading.

The quantity of ATP is determined for these samples: 50 µl of this dilution are placed in a luma-basin and 50 µl of luminol are added. The reading of luminescence starts after 10 seconds. Measurements are taken using a Biocounter M2010A LUMACâ/3M.

The results obtained express the percent increase of luminescence. This luminescence was measured after various incubation periods, in the cells treated with the active ingredient compared to the untreated cells, in the fibroblasts and in the adipocytes. This increase in luminescence expresses the increase in the quantity of intracellular ATP, luminescence being proportional to the quantity of ATP present in the cells.

|  | Times | | | |
|---|---|---|---|---|
|  | t = 5 min | t = 15 min | t = 30 min | t = 3 heures |
| on fibroblastes + active ingredient | +60%, | +75% | +45% | +0.2% |
| on adipocytes + active ingredient | +1% | +30% | — | +16% |

These results show that, in the presence of the peptide, the quantity of intracellular ATP increases significantly compared to the untreated cells. We observe this increase in luminescence in fibroblasts as well as in adipocytes, which means that the increase of ATP takes place in the two kinds of cells.

However, for fibroblasts the increase begins after 5 minutes and reaches its maximum 15 minutes after the administration of the active ingredient according to the invention, at which point they return approximately to their basal state after 2 hours. Whereas for adipocytes, the maximum is reached at 15 minutes after the application of the peptide, and the ATP level is maintained for at least 3 hours.

EXAMPLE 2

Demonstration of the Effect of the Peptide on the Protein Expression of the Extracellular Matrix The purpose of this study is to determine the influence of the peptide according to the invention on the ability of fibroblasts to synthesize fibronectin and collagen types I and III. The technique of immunofluorescence is used to accomplish this goal.

Immunofluorescence is a semi-quantitative technique which permits one to assess the level of each protein present in the cellular cytoplasm.

Human fibroblasts are cultured in Labteks then they are cultured overnight. When the cells reach between approximately 40 and 70% of confluence, they are rinsed with HBS buffer, and either a $10^{-6}$ M composition of the peptide sequence Arg-Gly-Ser, representative of the family of peptides according to the invention, or a control composition not containing peptide, is added. The cells are then incubated for 24 hours. After elimination of the supernatants and rinsing of the cultures, the cells are fixed with paraformaldheyde for 30 minutes at 4° C., then rinsed with PBS buffer. 200 mL of anti-fibronectin and/or anti-collagen I and/or anti-collagen III antibody is then added. Incubation lasts 30 minutes at room temperature. The supernatants are eliminated and the cells are rinsed with PBS. 200 mL of secondary antibody, coupled to a fluorescent marker (fluorescein) is then added. After 30 minutes incubation at room temperature, the supernatants are eliminated and the cells are rinsed with PBS. The slides are then assembled and examined under a fluorescent reverse microscope. The quantity of fibronectin and/or collagen I and/or III, synthesized by the cells, is proportional to the intensity of fluorescence.

The results obtained show that the addition of peptide to the fibroblast culture medium causes an increase in the synthesis of fibronectin and/or in the collagen I and III synthesis by the cells. The stimulation that was observed was significant.

Indeed, when the fibroblasts are incubated in the presence of a composition containing the peptide, an increase in the intensity of fluorescence occurs after 12 hours, compared to the untreated cells, thus representing a stimulation of the synthesis of fibronectin and/or a stimulation of the collagen I synthesis and/or a stimulation of the collagen III synthesis by the fibroblasts.

EXAMPLE 3

Effect of the Peptide on Keratin Expression by Immunofluorescence

The purpose of this study is to determine the influence of the peptide according to the invention on keratin synthesis, by keratinocytes, using the technique immunofluorescence. A study using the technique of immunofluorescence, identical to that of example 2, was carried out on HaCat human keratinocytes, with anti-keratin Pan cK antibodies.

The results obtained show that the addition of peptide of the sequence Arg-Gly-Ser, representative of the family of peptide according to the invention, in the culture medium of the keratinocytes has the effect of increasing keratin synthesis by the cells. The stimulation that was observed was significant. Indeed, when the keratinocytes are incubated in the presence of the composition containing the peptide, we observe an increase in the fluorescence intensity at 24 hours, representing the stimulation of keratin synthesis by the keratinocytes.

EXAMPLE 4

Demonstration of the Effect of Peptide on Cell Differentiation

The purpose of this study is to determine the influence of the peptide according to the invention, on cell differentiation, using the technique of immunofluorescence. The principle of this technique rests on the detection of cell differentiation markers such as involucrine and the ERG molecule.

A study, using the technique of by the immunofluorescence, identical to those of examples 2 and 3, was carried out on HaCat human keratinocytes, with anti-ERG 1-2 antibodies (the ERG 1-2 molecule is a marker of a very early stage of cell differentiation).

The results obtained show that the addition of peptide of the sequence Arg-Gly-Ser, representative of the family of the peptide according to the invention, in the culture medium of the keratinocytes increases the quantity of ERG molecules present in the cells. The stimulation that was observed was significant. Indeed, when the keratinocytes are incubated in the presence of the composition containing the peptide, we observe an increase in the intensity of fluorescence at 24 hours thus showing a stimulation of the synthesis of ERG molecules by the keratinocytes, which indicates an increase in the level of cell differentiation.

EXAMPLE 5

Activity of the Peptide on Adipocytes

1) Principle of the In-Vitro Test:

The effect of the peptide is evaluated by microscopic observations of the number and of the size of the lipid vacuoles present into the adipocytes after coloring. Adipocytes are incubated, or not incubated, in the presence of the peptide.

2) Experimental Model:

The demonstration of the biological activity of the active ingredient was carried out on the 3T3-L1 preadipocyte cell line, maintained in an adequate medium. Under some conditions, these preadipocytes are capable of entering the final phase of differentiation. The cells are cultured in Labteks and are maintained in DMEM containing 10% of FCS until they reach 100% confluence. Once at confluence, the cells are cultivated in traditional culture medium, containing differentiation inducers (IBMX, dexamethasone and insulin), in order to induce the final phase of differentiation and to thus obtain mature adipocytes. The adipocytes are then treated with peptide of the sequence Arg-Gly-Ser, representative of the family of peptide according to the invention, in a 1% solution of a 50 ppm solution. The adipocytes are incubated for different times: 30 minutes, 3 hours and 6 hours. After the different incubation period, the treated and untreated adipocytes are colored with "Oil Red" solution (Sigma, 0-0625). This solution is prepared by adding 0.5 g of the product to 100 mL of isopropanol and by subsequently making a 4/10 dilution of this solution in distilled water. Then, this final solution is filtered. The adipocytes are fixed for 10 minutes in a 4% formol solution and NaCl and the Red Oil solution is applied for 15 minutes. A 30 second counter-staining in Hematoxylin is possible. The cells are then rinsed with tepid water and are assembled on slides, in an absorbent medium (Aquatex). Observation is carried out using an optical microscope.

3) Results:

The results of the cell observation show that, contrary to the control conditions, control adipocytes (to which the active ingredient was not applied), have a spherical, bulky form and a significant accumulation of intracytoplasmic lipid vesicle. The mature adipocytes, treated with a solution containing the active ingredient according to the invention, are less round and their intra-adipocyte vesicle content is clearly reduced.

The solution containing the peptide according to the invention turns out to be particularly efficient in limiting the process of adipocyte hypertrophy most likely by increasing the phenomenon lipolysis. It thus permits the elimination of triglycerides contained in the intra-adipocyte vesicles.

These results are confirmed by measuring the quantity of glycerol released by the adipocytes in the surrounding medium, according to HPLC analysis, as well as with an enzymatic assay technique.

EXAMPLE 6

Activity of the Peptide on the Amount of Intracellular Camp

1) Principle of the Test:

The objective of this test is to measure the increase in the intracellular concentration of cAMP, in adipocytes, in order to determine the activation of the phenomenon of lipolysis.

Lipolysis is a mechanism which releases triglycerides contained in the adipocyte vacuoles. This reaction is carried out by the enzyme, Triglyceride-lipase, which hydrolyses triglycerides into free fatty acids and glycerol. These fatty acids are released in the extracellular medium and are eliminated in blood circulation. Triglyceride-lipase is controlled by the amount of intracellular cAMP. Thus, by increasing the amount of intracellular cAMP, we increase the activity of the enzyme allowing the hydrolysis of triglycerides thereby stimulating the phenomenon of lipolysis.

2) Experimental Model:

The test was carried out on cultured 3T3-L1 fibroblasts. Under the action of a hormone cocktail, these cells have the ability to differentiate into pre-adipocytes, then into adipocytes filled with triglycerides.

3T3-L1 cells are cultured on 24 well plates and are maintained until they reach 100% confluence in DMEM containing 10% of FCS. Once at confluence, the cells are cultivated in traditional culture medium, containing differentiation inducers (IBMX, dexamethasone and insulin), in order to induce the final phase of differentiation thereby obtaining mature adipocytes. The adipocytes are then treated with the peptide of sequence Arg-Gly-Ser, representative of the family of peptide according to the invention, in a 1% solution of a 50 ppm solution. A negative control test is realized in the presence of a solution not containing the active ingredient. The adipocytes are incubated, or not incubated, in the presence of the active ingredient being tested. The amount of intracellular cAMP is measured at different times (15 minutes, 30 minutes and 2 hours).

After the various incubation periods, in presence, or absence, of the active ingredient being tested, the amount of cAMP contained in the adipocytes is measured using the "AMP Biotraka EIA System" Kit purchased from Amersham Biosciences. At the end of incubation, the plates are emptied, then rinsed with cold PBS. The protocol for measuring the amount of cAMP is performed according to the instructions provided by the kit. The measurement of the quantity of cAMP is made reading the OD of the solutions at 450 nm (the cAMP level is proportional to the OD).

3) Results:

The results express the intracellular cAMP concentration, in nmol/mL, noted after different incubation times, as well as the percent increase in the concentration of cells treated with the active ingredient, compared to the untreated cells.

|  | Times | | | |
| --- | --- | --- | --- | --- |
|  | t = 0 | t = 15 min | t = 30 min | t = 2 h. |
| concentration nmol/mL | 226 | 246 | 304 | 287 |
| % of increase | — | +8.6% | +33% | +28% |

These results show that cells, in the presence of the active ingredient, have a significant increase in the amount of intracellular cAMP compared to untreated cells. This increase begins approximately at 5 minutes and reached its maximum 30 minutes after the administration of the peptide according to the invention. We observed no increase in the cAMP concentration in untreated cells.

This increase in the amount of cAMP in the adipocytes, combined with the results obtained in the example 5, lead us to conclude that the peptide according to the invention acts, on adipocytes, as well as on the mechanism of lipolysis. Indeed, by increasing the amount of cAMP in adipocytes, we increase the activity of Triglyceride-lipase, and we thus promote lipolysis. The peptide according to the invention promotes the elimination of triglycerides contained in the intra-adipocyte vesicles.

EXAMPLE 7

Preparation of Compositions

These compositions were obtained by a simple mixture of the various components. The quantities indicated are expressed as percent by weight.

| INCI names | Massic % |
| --- | --- |
| 1. Emulsion oil-in-water | |
| OILY PHASE | |
| Cetearyl Alcohol (and) Cetearyl Glucoside | 5.00 |
| Simmondsia Chimensis Seed Oil | 5.00 |
| Paraffinum Liquidum (Mineral oil) | 5.00 |
| Isopropyl Palmitate | 7.00 |
| AQUEOUS PHASE | |
| Glycerin | 5.00 |
| Allantoin | 0.10 |
| Arg-Gly-Ser peptide | 1.5 ppm |
| Polyacrylamide (and) C13-14 Isoparaffin (and) Laureth-7 | 0.30 |
| Conservative | 0.50 |
| Perfume (Fragrance) | 0.50 |
| Aqua (Water) | Qsp |
| 2. Lotion | |
| Propylene Glycol | 1.00 |
| Allantoin | 0.30 |
| Glycerin | 1.00 |
| PEG-7 Glyceryl Cocoate | 1.00 |
| Arg-Gly-Ser Peptide | 0.1 ppm |
| Conservative | 0.20 |
| Perfume (Fragrance) | 0.50 |
| Aqua (Water) | qsp |
| 3. Gel | |
| Carbomer | 25.00 |
| triethanolamine | 0.50 |
| Arg-Gly-Ser Peptide | 1 ppm |
| Conservative | 0.20 |
| Tetrasodium EDTA | 0.10 |
| Perfume (Fragrance) | 0.50 |
| Water-soluble Stain | Qsp |
| Aqua (Water) | Qsp |
| 4. Slimming Cream | |
| PHASE A | |
| Cetearyl Alcohol (and) Cetearyl Glucoside | 5.00 |
| Squalane | 2.50 |
| Isopropyl Palmitate | 3.50 |
| Octyldodecanol | 1.50 |
| Phenoxyethanol (and) Methylparaben (and) Ethylparaben (and) Butylparaben (and) Propylparaben (and) Isobutylparaben | 0.50 |
| PHASE B | |
| Aqua (Water) | Qsp |
| Glycerin | 3.00 |
| Butylene glycol | 3.00 |
| PHASE C | |
| Sodium Acrylate/Acryloyldimethyl Taurate Copolymer(and) Isohexadecane(and) Polysorbate 80 | 0.60 |
| PHASE D | |
| Arg-Gly-Ser Peptide | 1.25 ppm |
| Perfume (Fragrance) | Qsp |
| Colorant | Qsp |

The components of phase A are molten at 75° C. and the components of the phase are B heated to 75° C. The phase A is emulsified with B, then the mixture is cooled below 40° C. The phases C and D are then added under constant agitation.

| INCI names | Massic % |
|---|---|
| 5. Toning - Slimming Spray | |
| PHASE A | |
| Glyceryl Stearate (and) Ceteareth-20 (and) Ceteareth-12 (and) Cetearyl Alcohol | 4.60 |
| Ceteareth-20 | 1.40 |
| Dicaprylyl Ether | 3.00 |
| C12-C15 Alkyl Benzoate | 5.00 |
| Phenoxyethanol (and) Methylparaben (and) Ethylparaben (and) Butylparaben (and) Propylparaben (and) Isobutylparaben | 0.50 |
| Isononyl Isononanoate | 5.00 |
| Phenoxyethanol (and) Methylparaben (and) Ethylparaben (and) Butylparaben (and) Propylparaben (and) Isobutylparaben | 0.50 |
| PHASE B | |
| Aqua (Water) | 15.00 |
| Glycerin | 3.00 |
| PHASE C | |
| Aqua (Water) | Qsp |
| PHASE D | |
| Arg-Gly-Ser Peptide | 1.50 ppm |
| Perfume (Fragrance) | qsp |
| Water-soluble Stain | qsp |

The components of phase A and the phase B are heated separately at 65° C.; the phase B is incorporated in phase A under agitation. The temperature of the mixture is heated to 83° C. then it is cooled until a temperature of inversion of phase. The phase C is then added. The active ingredient is added when the temperature reached less than 40° C. It is then possible to add perfumes and/or dyes.

| INCI names | Massic % |
|---|---|
| 6. Toning - Slimming - anti-cellulitis Gel | |
| Carbomer | 25.00 |
| Aqua (Water) | Qsp |
| Methyl Propanediol | 3.00 |
| Tetrasodium EDTA | 0.10 |
| DMDM Hydantoin (and) Iodopropynyl butylcarbamate | 0.20 |
| Arg-Gly-Ser Peptide | 1.25 ppm |
| Triethanolamine | 0.50 |
| Perfume (Fragrance) | Qsp |
| Water-soluble Stain | Qsp |

The Carbopol gel is prepared at 2%. The ingredients are added in the order enumerated above, under agitation. The mixture is then neutralized with the TEA. Perfume and dyes are added if necessary.

The invention claimed is:

1. A method for treating or inhibiting a loss of elasticity, said method comprising administering to a subject in need thereof an effective amount of a cosmetic, dermatological, or pharmaceutical composition comprising an acceptable medium and a peptide of formula (I):

$$(AA)n\text{-}Arg\text{-}Gly\text{-}Ser\text{-}(AA)n \qquad (I),$$

wherein (AA) is an unspecified amino acid or derivative thereof, and n is an integer ranging between 0 and 3.

2. The method according to claim 1, wherein the peptide of formula (I) has the sequence Arg-Gly-Ser.

3. The method according to claim 1, wherein the peptide of formula (I) has a protective group, wherein the protective group is either an acylation of the amino-terminal, acetylation of the amino terminal, an amidation of the carboxy terminal, or esterification of the carboxy-terminal.

4. The method according to claim 1, wherein the peptide of formula (I) is present in the composition at a concentration ranging approximately between 0.005 and 500 ppm.

5. The method according to claim 1, wherein said composition is in a form for topical cutaneous application.

6. The method according to claim 1, wherein the peptide of formula (I) is solubilized in one or more solvents selected from the group consisting of water, ethanol, propanol, isopropanol, propylene glycol, butylene glycol, dipropylene glycol, ethoxylated diglycol, propoxylated diglycol, cyclic polyol, petroleum jelly, liposome, and a vegetable oil.

7. The method according to claim 1, wherein the peptide of formula (I) is solubilized in a liposome.

8. The method according claim 1, wherein the composition is in a form selected from the group consisting of an aqueous solution, hydroalcoholic solution, oily solution, oil-in-water emulsion, water-in-oil emulsion, multiple emulsions, cream, suspension, powders a milk, a serum, a pomade, a gel, a paste, a foam, and a stick.

9. The method according to claim 1, wherein the composition is administered topically.

10. The method according to claim 1, wherein said loss of elasticity comprises one or more manifestations selected from the group consisting of wrinkles, fine lines, limp skin, slackened skin, slimmer looking skin, loss of skin tone, dull skin, skin which lacks radiance, and orange-peel skin.

11. The method according to claim 1, wherein the peptide of formula (I) is adsorbed on powdered organic polymers or a mineral support.

12. The method according to claim 11, wherein the mineral support is selected from the group consisting of bentonite and talc.

13. A method for treating a loss of elasticity, said method comprising administering to a subject an effective amount of a cosmetic, dermatological, or pharmaceutical composition comprising an acceptable medium and a peptide of formula (I):

$$(AA)n\text{-}Arg\text{-}Gly\text{-}Ser\text{-}(AA)n \qquad (I),$$

wherein (AA) is an unspecified amino acid, and n is an integer ranging between 0 and 3, and
wherein said loss of elasticity comprises one or more manifestations selected from the group consisting of wrinkles, fine lines, limp skin, slackened skin, slimmer looking skin, loss of skin tone, dull skin, skin which lacks radiance, and orange-peel skin.

* * * * *